United States Patent [19]

Imai

[11] Patent Number: 4,479,025
[45] Date of Patent: Oct. 23, 1984

[54] ALKYLAROMATIC HYDROCARBON DEHYDROGENATION PROCESS

[75] Inventor: Tamotsu Imai, Mt. Prospect, Ill.

[73] Assignee: UOP Inc., Des Plaines, Ill.

[21] Appl. No.: 443,722

[22] Filed: Nov. 22, 1982

[51] Int. Cl.³ .............................................. C07C 5/36
[52] U.S. Cl. .................................. 585/441; 585/402; 208/134
[58] Field of Search ............... 585/440, 441, 442, 443, 585/444, 445, 402

[56] References Cited

U.S. PATENT DOCUMENTS

| | | | |
|---|---|---|---|
| 2,831,907 | 4/1958 | Mayfield et al. | 585/440 |
| 3,409,689 | 11/1968 | Ward | 585/441 |
| 3,515,765 | 6/1970 | Berger | 585/441 |
| 3,515,766 | 6/1970 | Root et al. | 260/669 |
| 3,515,767 | 6/1970 | Carson et al. | 585/441 |
| 3,702,346 | 11/1972 | Kellar | 260/669 R |
| 3,847,968 | 11/1974 | Hughes | 585/440 |
| 3,868,428 | 2/1975 | Cox | 260/669 R |
| 3,978,150 | 8/1976 | McWilliams, Jr. | 260/683.3 |
| 4,009,218 | 2/1977 | Uitti | 585/441 |
| 4,039,602 | 8/1977 | Uitti | 585/441 |
| 4,113,787 | 9/1978 | Ward | 585/441 |
| 4,288,234 | 9/1981 | Cox et al. | 585/441 |
| 4,338,476 | 7/1982 | Vickers et al. | 585/440 |

OTHER PUBLICATIONS

Article at pp. 519–528 of vol. 41 of The Transactions of The American Institute of Chemical Engineers (1945) by J. M. Mavity et al.

Primary Examiner—Delbert E. Gantz
Assistant Examiner—A. Pal
Attorney, Agent, or Firm—James R. Hoatson, Jr.; John F. Spears, Jr.; William H. Page, II

[57] ABSTRACT

A hydrocarbon conversion process is disclosed for the dehydrogenation of alkylaromatic hydrocarbons such as ethylbenzene or ethyltoluene. A subatmospheric pressure is maintained in the reaction zone by the use of two separate compressors. The first compressor pressurizes the vapor phase reactor effluent prior to the final indirect heat exchange step(s) used to partially condense this stream. The second compressor maintains the vapor-liquid separator which receives the partially condensed reactor effluent stream at a subatmospheric pressure. This facilitates operation of the reactor at a subatmospheric pressure.

11 Claims, 1 Drawing Figure

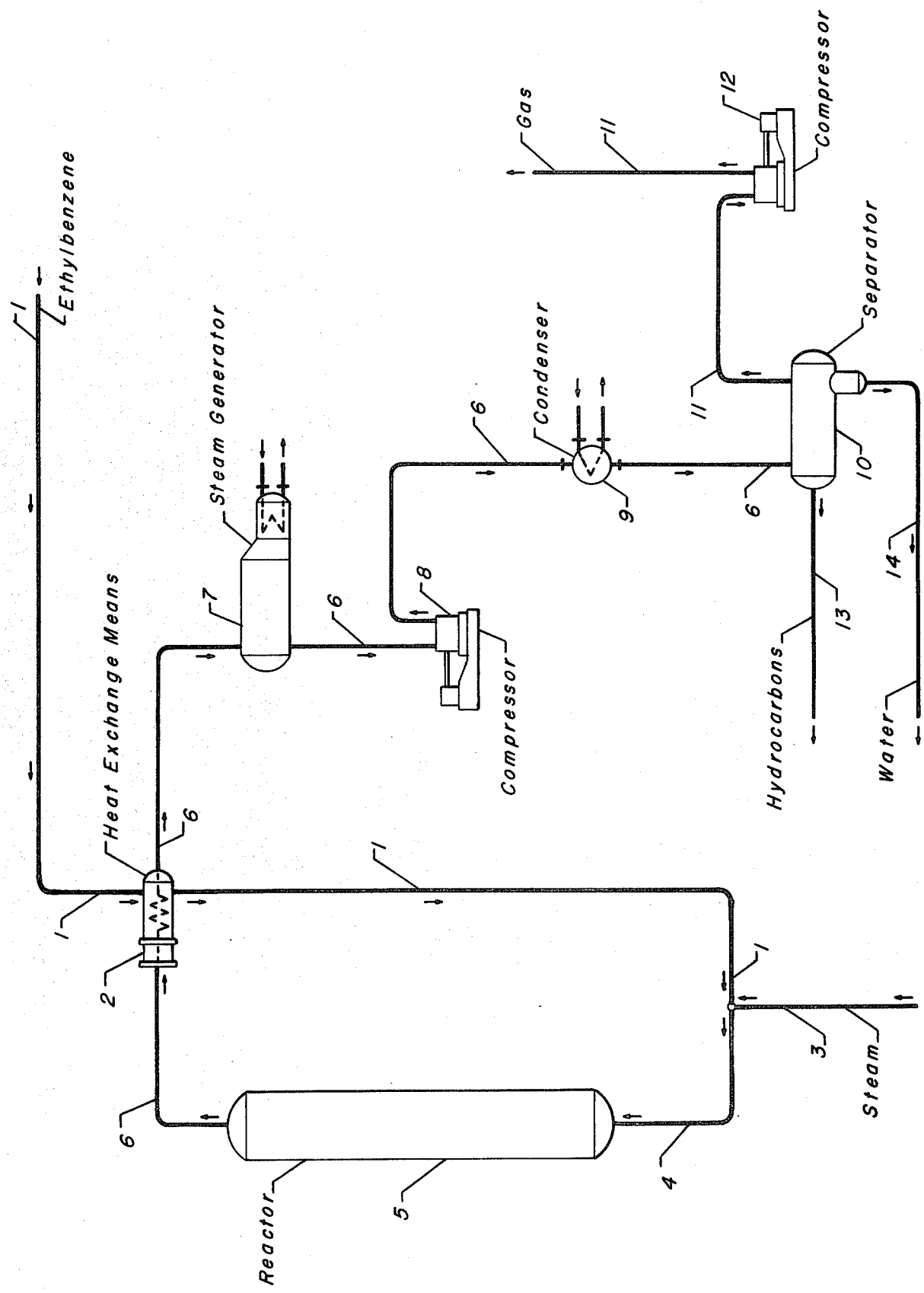

ALKYLAROMATIC HYDROCARBON DEHYDROGENATION PROCESS

FIELD OF THE INVENTION

The invention relates to the processing of hydrocarbons and more specifically to a process for the catalytic dehydrogenation of alkylaromatic hydrocarbons. The invention therefore relates to the synthesis of aromatic compounds, such as styrene, by dehydrogenation, with the dehydrogenation occurring in a number of sequential stages. The invention directly relates to an improved method for maintaining a subatmospheric pressure in the dehydrogenation reactor.

PRIOR ART

The dehydrogenation of hydrocarbons is well described in the prior art, with both acyclic and aromatic hydrocarbons being thereby converted to the corresponding less saturated products. For instance dehydrogenation is performed commercially for the production of styrene from ethylbenzene to fulfill the sizable demand for this polymer precursor. The product styrene may be polymerized with itself or it may be copolymerized with butadiene, isoprene, acrylonitrile, etc. Processes for the dehydrogenation of alkylaromatic hydrocarbons are often integrated with an alkylation process which produces the alkylaromatic hydrocarbons.

U.S. Pat. No. 3,515,766 issued to W. N. Root et al and U.S. Pat. No. 3,409,689 issued to D. J. Ward are pertinent for their showing of typical prior art catalytic steam dehydrogenation processes for alkylaromatics including ethylbenzene. These references describe the admixture of superheated steam into the feed hydrocarbon and the admixture of additional amounts of superheated steam with the reactants between sequential beds of dehydrogenation catalyst. These references also show an overall process flow into which the subject process could be integrated.

The use of a subatmospheric pressure in the reaction zone of an alkylaromatic hydrocarbon dehydrogenation process is known as shown by the teachings of U.S. Pat. Nos. 3,868,428 and 4,288,234. For instance, the latter of these patents teaches that the dehydrogenation zone is operated at a pressure in the order of from 2 to 25 psia. This reference is also pertinent for its showing of the use of a compressor on the discharge side of the dehydrogenation zone. However, this compressor is described as being located downstream of a cooling zone in which a liquid-phase crude aromatic hydrocarbon product stream is removed by condensation. The reference therefore seems to be similar in this regard to U.S. Pat. No. 3,702,346, in which a vacuum pump removes vapors from the phase separation vessel which receives the partially condensed dehydrogenation zone effluent stream.

The production of styrene by the low pressure dehydrogenation of ethylbenzene is described in detail in an article at pages 519–528 of volume 41 of *The Transactions of the American Institute of Chemical Engineers* (1945).

U.S. Pat. No. 3,978,150 is pertinent for its showing of a paraffin dehydrogenation process in which the reactor is operated at a substmospheric pressure. This pressure is maintained by vacuum source, which may be mechanical in nature, located in the line carrying the reactor effluent stream. A heat exchanger is located between the reactor and the vacuum source. This patent also indicates that a subatmospheric pressure separation of the product hydrocarbon could be performed.

BRIEF SUMMARY OF THE INVENTION

The invention provides a process for the dehydrogenation of alkylaromatic hydrocarbons in which it is more economical to achieve a desired subatmospheric pressure in the reaction zone. This improvement is accomplished by placing a compressing means in the effluent line of the reaction zone at a point upstream of the initial condensation of the heavier $C_6+$ hydrocarbons and water present in the dehydrogenation reaction zone effluent stream. A broad embodiment of the invention may therefore be characterized as a process for the dehydrogenation of an alkylaromatic hydrocarbon which comprises the steps of contacting a reactant stream comprising an alkylaromatic hydrocarbon with a catalyst maintained at dehydrogenation conditions which include a subatmospheric pressure and thereby forming a vapor-phase dehydrogenation zone effluent stream comprising the alkylaromatic hydrocarbons, an unsaturated product hydrocarbon, hydrogen and steam; cooling the dehydrogenation zone effluent stream without affecting significant condensation by indirect heat exchange against the reactant stream; compressing the dehydrogenation zone effluent stream to a higher pressure which is less than one atmosphere absolute by means of a first mechanical compressing means; partially condensing the dehydrogenation zone effluent stream; separating the resultant mixed-phase dehydrogenation zone effluent stream in a vapor-liquid separation zone, maintained at a pressure less than one atmosphere absolute through the use of a second mechanical compresssing means, into a vapor-phase process stream comprising hydrogen and a liquid-phase process stream; and recovering the unsaturated product hydrocarbon from the liquid phase process stream.

BRIEF DESCRIPTION OF THE DRAWING

The Drawing is a schematic illustration of the reaction section of a process for the dehydrogenation of ethylbenzene to produce styrene. Referring now to the Drawing, a feed stream comprising ethylbenzene is heated by indirect heat exchange in the feed effluent heat exchange means 2 and then continues through line 1 to be admixed with a stream of superheated steam from line 3. This admixture of steam and ethylbenzene passes into the bottom of the reactor 5 through line 4. The reactants pass upward through the reactor preferably making three or more passes through different beds of dehydrogenation catalyst maintained at dehydrogenation conditions which include a subatmospheric pressure. The reactants may be heated within the reactor by means not shown.

The contacting of the ethylbenzene with the dehydrogenation catalyst contained within the reactor produces a reaction zone effluent stream carried by line 6 which comprises unreacted ethylbenzene, styrene, steam and hydrogen. This effluent stream is cooled in the feed effluent heat exchange means 2 and by passage through a steam generator 7, with this heat exchange extracting only sensible heat from the effluent stream and producing no significant condensation of water, ethylbenzene or styrene. The still vapor-phase effluent stream is then compressed in the first compressor 8 to a higher pressure which preferably is still less than 1 atmosphere absolute. The effluent stream continues through line 6 and is then partially condensed in the condenser 9 to produce a mixed-phase stream. This stream is separated in the vapor-liquid separator 10 into a first liquid phase of water containing dissolved hydrocarbons, a hydrocarbon liquid phase and a vapor phase. The vapor phase comprising hydrogen and low temperature water vapor is removed from the separator through line 11 through the use of a second compressor 12. The hydrocarbons are withdrawn through line 13 and preferably passed to the appropriate fractional distillation facilities for the recovery of the product styrene. The condensed water is decanted from the separator through line 14.

This illustration of one possible process flow which may be utilized with the subject invention is not intended to thereby limit the scope of the invention, which may be practiced with the other process flows set out herein or in other variations not described herein.

DETAILED DESCRIPTION

Processes for the dehydrogenation of aromatic hydrocarbons are in widespread commercial use. For instance, large quantities of styrene are produced by the dehydrogenation of ethylbenzene. The resultant styrene may be polymerized with itself or it may be copolymerized with butadiene, isoprene, acrylonitrile, etc. Other hydrocarbons which may be dehydrogenated in much the same manner include diethylbenzene, ethyltoluene, propylbenzene and isopropylbenzene. However, since the great majority of the present commercial dehydrogenation processes are employed for the dehydrogenation of ethylbenzene, the following description of the subject invention will be presented primarily in terms of the dehydrogenation of ethylbenzene. This is not intended to exclude from the scope of the subject invention those other alkylaromatic hydrocarbons set out above or those having different ring structures including bicyclic compounds.

The dehydrogenation reaction releases hydrogen thereby increasing the number of molecules present compared to the number in the feed stream. The dehydrogenation reaction is therefore favorably influenced by a decrease in pressure. Accordingly most commercial dehydrogenaton processes operate at a relatively low pressure for hydrocarbon conversion processes, and as pointed out in the previously cited references, it is known that the use of subatmospheric pressures would be desirable. Despite this knowledge, it is believed that the present commercial operations normally employ a pressure in the dehydrogenation zone which is close to atmospheric pressure rather than significantly below it. The basic reasons for this are the expense and difficulty of maintaining the dehydrogenation zone at subatmospheric pressures on the order of 0.75 atmosphere absolute or below. One of the major causes of this difficulty in economically obtaining the desired low pressures is the pressure drop which is inherent in the flow of the reactants through the reactor and the subsequent indirect heat exchange means of the dehydrogenation zone. More specifically, it is common practice to maintain the dehydrogenation reaction zone at a low pressure by withdrawing a vapor stream from the product settler (vapor-liquid separator), as by a steam jet ejector. The vacuum is "pulled" at this point since the condensation has greatly reduced the amount of vapor which remains, and it is necessary to have the reactor effluent flow toward the product separator. In a commercial scale process, there is a very high flow rate of the feed hydrocarbon and any diluent such as steam through the total apparatus including the transfer lines and heat exchangers. The cumulative pressure drops in these devices due to this high flow rate are such that even though the products settler is at a mildly subatmospheric pressure, the reaction zone itself will be at a pressure equal to or above one atmosphere absolute. This effect can be reduced by judicious equipment design but cannot be eliminated. Therefore, it becomes necessary to maintain a commercially impractical vacuum in the product separator to hold the reactor at a substmospheric pressure in this manner.

It is therefore an objective of the subject invention to provide a process for the dehydrogenation of alkylaromatic hydrocarbons in which the reaction zone is maintained at a subatmospheric pressure. It is a further objective of the subject invention to provide a process for the dehydrogenation of ethylbenzene or ethyltoluene in which it is more economical to maintain the reaction zone at a pressure which is significantly below atmospheric pressure.

In the subject process a mechanical compression means is utilized at a point upstream of the products settler or vapor-liquid separator to maintain the desired low pressure within the reaction zone. More specifically this mechanical cmpression means is located upstream of the indirect or direct heat exchange means utilized to condense the very great majority of the $C_6+$ hydrocarbons present in the reaction zone effluent stream. This compression means is preferably located downstream of any indirect heat exchange means which are utilized to recover sensible heat from the reaction zone effluent stream but is located upstream, that is closer to the reaction zone, of the means utilized to condense the product hydrocarbon. This location is significant since the preferred indirect heat exchange means utilized to effect the condensation is the source of a very significant amount of the total pressure drop through the reactant flow path. The provision of a compression means at this location thereby avoids the pressure drop through this condensing means.

The compression means utilized upstream of the condensing means is not the sole means utilized to maintain the desired reduced pressure within the reaction zone. This compression means therefore operates in cooperation with a second compression means which preferably is utilized to remove the vapor stream from the vapor-liquid separator much in the same manner employed in the prior art. This downstream compression means functions to maintain a low pressure on the discharge side of the upstream compression means, thereby reducing the compression ratio across the upstream compression means and reducing the utilities cost of operating the upstream compression means. It is therefore preferred that the pressure on the discharge side of the first or upstream compression means is less than 1 atmosphere absolute. It is also preferred that the vapor-liquid separation zone is maintained at a pressure less than 1 atmosphere absolute.

The dehydrogenation zone effluent stream is cooled by indirect heat exchange means prior to entering the first compression means. Preferably, this heat is utilized to heat the feed hydrocarbon entering the dehydrogenation zone and to generate steam in the manner illustrated in the Drawing. This initial heat exchange and cooling of the dehydrogenation zone effluent stream is to be performed without any significant condensation of either water of $C_6+$ hydrocarbons present in the dehydrogenation zone effluent stream. As the term "significant condensation" is used herein, it is intended to indicate the condensation of more than 5 mole precent of any particular compound or class of compounds. It is therefore preferred that the dehydrogenation zone effluent stream is a totally vaporphase stream when it enters the first or upstream compression means. The initial indirect heat exchange recovers the valuable high temperature sensible heat present in the effluent stream and cools the effluent stream thereby increasing the density of this vapor-phase stream and lowering the operating temperature of the first compression means. It is preferred that the effluent stream is cooled at least 400 and more preferably at least 600 Fahrenheit degrees before being passed into the first compressing means. Any commercially suitable type of mechanical compression means may be employed as the first or second compression means, with the use of centrifugal compressors being preferred.

A preferred embodiment of the invention may therefore be characterized as a process for the dehydrogenation of an alkylaromatic hydrocarbon which comprises the steps of contacting a reactant stream comprising an alkylaromatic hydrocarbon with a plurality of beds of dehydrogenation catalyst maintained at dehydrogenation conditions which include a subatmospheric pressure and the presence of steam and thereby forming a dehydrogenation zone effluent stream comprising the alkylaromatic hydrocarbon, an unsaturated product hydrocarbon, hydrogen and steam; cooling the dehydrogenation zone effluent stream by indirect heat exchange against the reactant stream without significant condensation of water or the alkylaromatic hydrocarbon; compressing the dehydrogenation zone effluent stream in a first mechanical compressing means to a higher pressure less than 1 atmosphere absolute; partially condensing the dehydrogenation zone effluent stream by indirect heat exchange and thereby producing a mixed-phase process stream; separating the mixed-phase process stream in a vapor-liquid separation zone, maintained at a pressure less than 1 atmosphere absolute through the use of a second mechanical compressing means, into a vapor-phase process stream comprising hydrogen and a liquid-phase process stream; and recovering the unsaturated product hydrocarbon from the liquid-phase process stream, and withdrawing the vapor-phase process stream through the use of a second compressing means.

As used herein, the term "dehydrogenation zone" is intended to refer to the total reactor system which contains the dehydrogenation catalyst. This catalyst may be divided into ten or more separate beds, but the dehydrogenation zone preferably comprises two or three catalyst beds with means for the intermediate addition and admixture of steam and possibly an oxygen supply steam. Suitable systems for this may be patterned after those presented in U.S. Pat. Nos. 3,498,755, 3,515,763 and 3,751,232. The catalyst beds may be contained in separate reaction vessels and may have either a cylindrical or an annular shape. The use of radial flow catalyst beds in a stacked configuration in a single overall vessel is preferred. Different dehydrogenation catalysts may be used in different beds as described in U.S. Pat. No. 3,223,743. Dehydrogenation catalysts generally consist of one or more metallic components selected from Groups VI and VIII of the Periodic Table. One typical catalyst for the dehydrogenation of alkylaromatics comprises 85% by weight ferric oxide, 2% chromia, 12% potassium hydroxide and 1% sodium hydroxide. A second dehydrogenation catalyst, which is used commercially, consists of 87–90% ferric oxide, 2–3% chromium oxide and from 8–10% potassium oxide. A third typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, which describes the manufacture of a catalytic composite of at least 35 wt. % iron oxide as an active catalytic agent, from about 1–8 wt. % zinc or copper oxide, about 0.5–50 wt. % of an alkali promoter, and from about 1–5 wt. % chromic oxide as a stabilizer and a binding agent.

Dehydrogenation conditions in general include a temperature of about 538° to about 1000° C. (1000°–1832° F.) and preferably about 565° to about 675° C. (1050°– F.). When ethylbenzene is being dehydrogenated, the space velocity, the rate of steam admixture and the inlet temperature are preferably adjusted to result in the effluent of each catalyst bed having a temperature of about 593° C. The temperature required for efficient operation of any specific dehydrogenation process will depend on the feed hydrocarbon and the activity of the catalyst employed. The pressure maintained within the dehydrogenation zone may range from about 100 to about 750 mm Hg, with a preferred range of pressures being from 250 to 700 mm Hg. The operating pressure within the dehydrogenation zone is measured at the inlet, midsection, and outlet of the zone to thereby provide an approximately average pressure. The combined feed stream is charged to the dehydrogenation zone at a liquid hourly space velocity, based on liquid hydrocarbon charge at 60° F., of about 0.1 to about 2.0 hr$^{-1}$, and preferably from 0.2 to 1.0 hr$^{-1}$.

The alkylaromatic hydrocarbon to be dehydrogenated is preferably admixed with superheated steam to counteract the temperature lowering effect of the endothermic dehydrogenation reaction. The presence of steam has also been described as benefiting the stability of the dehydrogenation catalyst by preventing the accumulation of carbon deposits. Preferably, the steam is admixed with the other components of the feed stream at a rate of about 0.8 to about 1.7 pound of steam per pound of feed hydrocarbon. Other quantities of steam may be added after one or more subsequent beds if desired. However, the dehydrogenation zone effluent stream should contain less than about 3 pounds of steam per pound of product hydrocarbon and preferably less than 2 pounds of steam per pound of product hydrocarbon.

The effluent stream removed from the dehydrogenation zone is normally quickly heat exchanged for the dual purposes of lowering its temperature to prevent polymerization of the styrene and for the recovery of heat. The effluent stream may be heat exchanged against a stream of steam, a reactant stream of this or another process or used as a heat source for fractionation, etc. Commercially, the effluent stream is often passed through several heat exchangers thereby heating a number of different streams. This heat exchange is performed subject to the constraints set out above. The heat exchange performed downstream of the first compression means should cool the dehydrogenation zone effluent stream sufficiently to affect the condensation of at least 95 mole percent of the feed and product hydrocarbons and also at least 95 mole percent of the water vapor. The use of a quench zone to accomplish this condensation is not preferred. Essentially all of the styrene or other product hydrocarbon, most water and other readily condensible compounds present in the effluent stream are thereby converted to liquids. This produces a mixedphase stream which is passed into a phase separation vessel. This procedure allows the facile crude separation by decantation of the hydrocarbons from the water and hydrogen present in the effluent stream. The styrene present in the dehydrogenation zone effluent stream becomes part of a hydrocarbon stream which is withdrawn from the separation vessel and transferred to the proper separation facilities. Preferably, the styrene is recovered from the hydrocarbon stream by using one of the several fractionation systems known in the art. This fractionation will preferably yield a relatively pure stream of ethylbenzene, which is recycled, and an additional stream comprising benzene and toluene. These two aromatic hydrocarbons are by-products of the dehydrogenation reaction. They may be recycled in part as taught in U.S. Pat. No. 3,409,689 and British Pat. No. 1,238,602 or entirely rejected from the process. Styrene is recovered as a third stream, which is withdrawn from the process. If desired, methods other than fractionation may be used to recover the styrene. For instance, U.S. Pat. No. 3,784,620 teaches the separation of styrene and ethylbenzene through the use of a polyamide permeation membrane such as nylon-6 and nylon 6,10. U.S. Pat. No. 3,513,213 teaches a separatory method employing liquid-liquid extraction in which anhydrous silver fluoroborate is used as the solvent. Similar separatory methods utilizing cuprous fluoroborates and cuprous fluorophosphates are described in U.S. Pat. Nos. 3,517,079; 3,517,080 and 3,517,081.

The recovery of styrene through the use of fractionation is described in several references including U.S. Pat. No. 3,525,776. In this reference, the hydrocarbonaceous phase removed from the phase separation zone is passed into a first column referred to as a benzenetoluene column. This column is operated at a subatmospheric pressure to allow its operation at lower temperatures and hence reduce the rate of styrene polymerization. Various inhibitors such as elemental sulfur, 2,4-dinitrophenol or a mixture of N-nitroso diphenyl amine and a dinitroso-o-cresol are injected into the column for this same purpose. Preferably, sulfur is also introduced into this column by returning at least a portion of the high molecular weight material separated from the bottoms stream of a styrene purification column. A more detailed description of this is contained in U.S. Pat. Nos. 3,476,656; 3,408,263 and 3,398,063. There is effected within the benzene-toluene column a separation of benzene and toluene from the effluent to produce an overhead stream which is substantially free of styrene and ethylbenzene. This stream preferably contains at least 95 mole percent benzene and toluene. The bottoms of the benzene-toluene column is passed into a second fractionation column from which ethylbenzene is removed as an overhead product and recycled. The bottoms stream of this column is then purified to obtain the styrene.

The endothermic nature of the dehydrogenation reaction results in a quick cooling of the reactants as they pass through the beds of dehydrogenation catalyst. This reduces the achievable conversion. For this reason the predominant commercial processes include some form of interstage heating between the separate beds of dehydrogenation catalyst. This heating may be by indirect heat exchange or by the addition of a very hot vapor which is normally superheated steam. Continuous heating by indirect heat exchange may also be employed. In more limited embodiments of the subject process, at least a portion of the interstage heating is obtained by the catalytically promoted oxidation of hydrogen. This not only reheats the feed hydrocarbon but also reduces the hydrogen concentration in the reactant stream and thereby promotes increased conversion. Any heat input by hydrogen combustion reduces the heat which must be supplied by other means. In the preferred use of superheated steam, the use of partial hydrogen combustion therefore reduces the amount of steam which is required. This in turn reduces the utilities cost of operating the process since less superheated steam must be produced and less water vapor must be condensed for removal from the dehydrogenation zone effluent stream.

The oxygen consumed during the hydrogen combustion is preferably admixed into the reactant stream at the point of interstage heating as part of an oxygen supply stream. The oxygen supply stream may be air but is preferably a gas having a higher oxygen content than air. It is preferred that the oxygen supply stream has a nitrogen content less than 10 mole percent, with the use of substantially pure oxygen being preferred if it is economically viable. The preferred oxygen concentration in the oxygen supply stream is primarily a matter of economics and would be determined by a comparison of the advantage of having pure oxygen to the cost of obtaining the oxygen. The basic disadvantages of the presence of nitrogen are the dilution of the hydrogen-containing gas stream removed from the product separation vessel and the fact that the nitrogen passes through the dehydrogenation zone thereby increasing the pressure drop through the catalyst bed and the absolute pressure being maintained within the dehydrogenation zone. On the other hand, the presence of nitrogen favorably affects the equilibrium conversion level by acting as a diluent.

The oxidation catalyst employed in the subject process to promote the interstage hydrogen oxidation may be any commercially suitable catalyst which meets the required standards for stability and activity and which possesses high selectivity for the oxidation of hydrogen as compared with the oxidation of the feed or product hydrocarbon. That is, the oxidation catalyst must have a high selectivity for the oxidation of hydrogen with only small amounts of the feed or product hydrocarbon being oxidized. The oxidation catalyst will have a different composition than the dehydrogenation catalyst. The preferred oxidation catalyst comprises a Group VIII noble metal and a metal or metal cation which possesses a crystal ionic radius greater than 1.35 Å, with both of these materials being present in small amounts on a refractory solid support. The preferred Group VIII metals are platinum and palladium, but the use of ruthenium, rhodium, osmium and iridium is also contemplated. The Group VIII metal is preferably present in an amount equal to 0.01 to 5.0 wt. % of the finished catalyst. The metal or metal cation having a radius greater than 1.35 Å is preferably chosen from Groups IA or IIA and is present in an amount equal to about 0.01 to about 20 wt. % of the finished catalyst. This component of the catalyst is preferably barium, but the use of other metals including rubidium or cesium is also contemplated.

The preferred solid support is alumina having a surface area between 1 and 300 m²/g, an apparent bulk density of between about 0.2 and 1.5 g/cc, and an average pore size greater than 20 Å. The metal-containing components are preferably impregnated into solid particles of the solid support by immersion in an aqueous solution followed by drying and calcination at a temperature of from about 500° to 600° C. in air. The support may be in the form of spheres, pellets or extrudates. The total amount of oxidation catalyst present within the dehydrogenation zone is preferably less than 30 wt. % of the total amount of dehydrogenation catalyst and more preferably is between 5 and 15 wt. % of this total amount of dehydrogenation catalyst.

The conditions utilized during the contacting of the reactant streams with the different beds of oxidation catalyst will be set to a large extent by the previously referred to dehydrogenation conditions. The preferred outlet temperature of any bed of oxidation catalyst is the preferred inlet of the immediately downstream bed of dehydrogenation catalyst. The temperature rise across any bed of oxidation catalyst is preferably less than 80 Centigrade degrees. The liquid hourly space velocity, based on the liquid hydrocarbon charge at 60° F., is preferably between 2 and 10 hr$^{-1}$. It is preferred that substantially all of the oxygen which enters a bed of oxidation catalyst is consumed within that bed of oxidation catalyst and that the effluent stream of any bed of oxidation catalyst contains less than 0.1 mole percent oxygen. The total moles of oxygen charged to the dehydrogenation zone is preferably less than 60% of the total moles of hydrogen available within the dehydrogenation zone for combustion and is therefore dependent on the conversion achieved in the dehydrogenation zone and the amount of hydrogen lost in solution or in any off-gas streams. This available hydrogen is the sum of any hydrogen recycled to the dehydrogenation zone and the hydrogen produced in all but the last bed of dehydrogenation catalyst. Preferably the oxygen charged to the dehydrogenation zone is equal to about 20 to 50 mole percent of the thus-defined available hydrogen. As used herein, the term "substantially all" is intended to indicate a major fraction of the indicated chemical compound(s) which have been acted upon in the manner described, with this major fraction preferably being over 90 mole percent and more preferably over 95 mole percent. As previously mentioned, the subject process is not limited to the production of styrene and may be used to produce paramethylstyrene by dehydrogenating ethyltoluene or for the production of other unsaturated product hydrocarbons.

I claim as my invention:

1. A process for the dehydrogenation of an alkylaromatic hydrocarbon which comprises the steps of:
   (a) contacting a reactant stream comprising an alkylaromatic hydrocarbon with a dehydrogenation catalyst maintained at dehydrogenation conditions which include a subatmospheric pressure and thereby forming a vapor-phase dehydrogenation zone effluent stream comprising the alkylaromatic hydrocarbon, an unsaturated product hydrocarbon and hydrogen;
   (b) cooling the dehydrogenation zone effluent stream without significant condensation of either water or C$_6$+hydrocarbons and not more than 5 mole percent of any compound or class of compounds by indirect heat exchange against the reactant stream;
   (c) compressing the dehydrogenation zone effluent stream to a higher pressure less than 1 atmosphere absolute by means of a first mechanical compressing means;
   (d) partially condensing the dehydrogenation zone effluent stream;
   (e) separating the resultant mixed-phase dehydrogenation zone effluent stream in a vapor-liquid separation zone, maintained at a pressure less than 1 atmosphere absolute through the use of a second mechanical compressing means, into a vapor-phase stream comprising hydrogen and a liquid-phase process stream; and (f) recovering the unsaturated product hydrogenation from the liquid-phase process stream.

2. The process of claim 1 further characterized in that the hydrogenation zone effluent stream is cooled by at least 400 Fahrenheit degrees prior to being compressed in the first compressing means.

3. The process of claim 2 further characterized in that the alkylaromatic hydrocarbon is ethylbenzene and the unsaturated product hydrocarbon is styrene.

4. The process of claim 2 further characterized in that the alkylaromatic hydrocarbon is ethyltoluene and the unsaturated product hydrocarbon is methyl styrene.

5. The process of claim 2 further characterized in that the reactant stream comprises steam.

6. The process of claim 5 further characterized in that the reactant stream is contacted with at least two separate beds of dehydrogenation catalyst and in that the reactant stream is heated at an intermediate point between two beds of dehydrogenation catalyst by the oxidation of hydrogen.

7. A process for the dehydrogenation of an alkylaromatic hydrocarbon which comprises the steps of:
   (a) contacting a reactant stream comprising an alkylaromatic hydrocarbon with a plurality of beds of dehydrogenation catalyst maintained at dehydrogenation conditions which include a subatmospheric pressure and the presence of steam and thereby forming a dehydrogenation zone effluent stream comprising the alkylaromatic hydrocarbon, an unsaturated product hydrocarbon, hydrogen and steam;
   (b) cooling the dehydrogenation zone effluent stream by indirect heat exchange against the reactant stream without significant condensation of either water or C$_6$+hydrocarbons and not more than 5 mole percent of any compound or class of compounds;
   (c) compressing the dehydrogenation zone effluent stream in a first mechanical compressing means to a higher pressure less than 1 atmosphere absolute;
   (d) partially condensing the dehydrogenation zone effluent stream by indirect heat exchange and thereby producing a mixed-phase process stream;
   (e) separating the mixed-phase process stream in a vaporliquid separation zone, maintained at a pressure less than 1 atmosphere absolute through the use of a second mechanical compressing means, into a vapor-phase process stream comprising hydrogen and which is withdrawn through the second compressing means and a liquid-phase process stream; and,
   (f) recovering the unsaturated product hydrocarbon from the liquid-phase process stream.

8. The process of claim 7 further characterized in that the reactant stream is heated at an intermediate point between separate beds of dehydrogenation catalyst by the catalytically promoted oxidation of hydrogen.

9. The process of claim 8 further characterized in that the unsaturated product hydrocarbon is para-methylstyrene.

10. The process of claim 8 further characterized in that the unsaturated product hydrocarbon is styrene.

11. The process of claim 8 further characterized in that the dehydrogenation zone is cooled at least 400 Fahrenheit degrees prior to being compressed in the first compressing means.

* * * * *